(12) United States Patent
Werner

(10) Patent No.: US 12,181,355 B2
(45) Date of Patent: Dec. 31, 2024

(54) METHOD FOR IDENTIFYING A CONNECTION, AND RINSING DEVICE

(71) Applicant: OLYMPUS Winter & Ibe GmbH, Hamburg (DE)

(72) Inventor: Alexander Werner, Bielefeld (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 344 days.

(21) Appl. No.: 17/835,177

(22) Filed: Jun. 8, 2022

(65) Prior Publication Data

US 2022/0397474 A1    Dec. 15, 2022

(30) Foreign Application Priority Data

Jun. 9, 2021   (DE) .................... 10 2021 114 775.1

(51) Int. Cl.
| | |
|---|---|
| *G01L 19/00* | (2006.01) |
| *A61B 90/70* | (2016.01) |
| *B08B 9/032* | (2006.01) |
| *G01L 7/00* | (2006.01) |

(52) U.S. Cl.
CPC .......... *G01L 19/0007* (2013.01); *A61B 90/70* (2016.02); *B08B 9/0325* (2013.01); *G01L 7/00* (2013.01); *A61B 2090/701* (2016.02); *B08B 2209/032* (2013.01)

(58) Field of Classification Search
CPC ...................... G01L 19/007; A61B 2090/701
See application file for complete search history.

(56) References Cited

U.S. PATENT DOCUMENTS

| | | | |
|---|---|---|---|
| 2007/0100204 A1* | 5/2007 | Feld .......................... | A61L 2/18 600/117 |
| 2007/0100206 A1 | 5/2007 | Lin et al. | |
| 2018/0020905 A1 | 1/2018 | Chouinard et al. | |
| 2018/0103830 A1* | 4/2018 | Thate .................. | G01M 3/2846 |

FOREIGN PATENT DOCUMENTS

DE    10 2012 020 934 A1    4/2014

* cited by examiner

*Primary Examiner* — Eric S. McCall
(74) *Attorney, Agent, or Firm* — Scully, Scott, Murphy & Presser, P.C.

(57) ABSTRACT

A method for identifying a connection between a first channel and at least one second channel located in a rinsing device. The method including: applying a first testing pressure to the first channel; reading in a first pressure signal representing a first pressure in the at least one second channel; and detecting the connection between the first channel and the at least second channel when the first pressure is one or more of at a predetermined first ratio to the testing pressure and above a predetermined first threshold.

19 Claims, 10 Drawing Sheets

| | 705 | 710 | 715 | 720 | 725 | 730 |
|---|---|---|---|---|---|---|
| | 0 | 0 | 0 | 0 | 0 | 0 |
| | 0 | 0 | 1 | 0 | 0 | 0 |
| | 0 | 1 | 0 | 0 | 0 | 0 |
| | 0 | 0 | 0 | 0 | 1 | 0 |
| | 0 | 0 | 0 | 1 | 0 | 0 |
| | 0 | 0 | 0 | 0 | 0 | 0 |

FIG 7

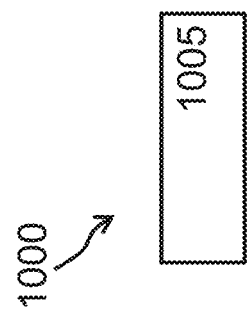

METHOD FOR IDENTIFYING A CONNECTION, AND RINSING DEVICE

CROSS-REFERENCE TO RELATED APPLICATION

The present application is based upon and claims the benefit of priority from DE 10 2021 114 775.1 filed on Jun. 9, 2021, the entire contents of which is incorporated herein by reference.

BACKGROUND

Field

The present disclosure relates to a method for identifying a connection, a method for cleaning a channel element, and a rinsing device.

Prior Art

Inside a cleaning and disinfecting device (CDD-E) for reprocessing endoscopes, in the case of pulsing rinsing methods, which alternately apply at least two different pressure levels to the loaded ware, e.g., water/air or water/water, resurge effects occur in the recirculation circuit when the loaded ware has at least one channel branch. These resurges can lead to premature failures of components in the rinsing circuit, since they are typically not configured for such a sudden stress. For example, a recirculation pump could lead to a premature failure of the device (CDD-E) due to damage. A plurality of endoscopes, however, have such channel branches, which are present at least in the biopsy channel. Here, two channels branch off, of which at least one channel is connected to the cleaning and disinfecting device (CDD-E) at the connection plug of the endoscope and an additional channel is connected to the cleaning and disinfecting device (CDD-E) at the operating part. Inside the operating part, the two channel pieces are joined together and are configured as only one channel until the distal end.

SUMMARY

It is an object to create an improved method for identifying a connection, an improved method for cleaning a channel element, and an improved rinsing device.

Such object can be solved by a method for identifying a connection, a method for cleaning a channel element, and a rinsing device having the features of the independent claims. Advantageous embodiments and developments are apparent from the following dependent claims.

Exemplary advantages that can be achieved are that, in a rinsing device, an existing fluidic connection between a first and at least one second channel element can be identified or detected. This enables channel branches in endoscope channels to be detected without the use of a non-return valve.

Also provided is a method for identifying a connection between a first and at least one second channel element located in a rinsing device, wherein the method comprises:
  applying a testing pressure to the first channel element;
  reading in a pressure signal which represents a pressure in the second channel element; and
  detecting the connection between the first and the at least second channel element when the pressure is at a predetermined ratio to the testing pressure and/or above a threshold.

A rinsing device is also provided for cleaning, disinfecting, and reprocessing minimally invasive surgical instruments. The minimally invasive surgical instrument can be, for example, an endoscope. For example, the endoscope has two channel elements: one operating part and one connection plug. The two channel elements of the surgical instrument are coupled to each other via a (fluidic) connection. The (fluidic) connection can be, for example, a hose which lets a fluid pass between the first and second channel elements. To test the connection between the two channel elements, a testing pressure is applied to a first channel element. The testing pressure can be, for example, compressed air with an increased pressure compared to an ambient pressure. The pressure is then identified in the second channel element. When the pressure in the second channel element corresponds with the testing pressure or respectively is above a threshold of the testing pressure, a fluidic connection can be assumed to exist between the two channel elements of the surgical instrument.

The approach presented here can also be referred to as a method for automatically detecting channel branches in the case of narrow-lumened loaded ware (surgical instruments like for example endoscopes) inside a cleaning and disinfecting device (CDD-E).

Thus, a method is described that enables channel branches in endoscope channels or in channel elements of surgical instruments to be detected in order to prevent a resurge effect on the pump installed in the rinsing circuit during drainage routines or compressed air/water cycles without requiring the use of non-return valves in the rinsing circuit, which can also be problematic from a hygienic perspective.

The approach presented here also enables that, in the case of a pulsation with compressed air during a pre-rinsing step, compressed air does not need to be applied to all branched channels simultaneously, meaning in parallel. A backflow preventer is also not provided at a given location in each channel that is supplied. If no information is available to the rinsing device regarding which channels are connected, meaning branched, with each other, the present system can still detect which channels have a branch with other channels.

The approach presented here also enables that a simultaneous, parallel pulsing of all channels of a level is not necessary to prevent an individual application, a feedback into the liquor supply branch and thus a pressure surge to the recirculation pump from taking place. The use of non-return valves can be prevented in this way, which would be problematic when using conventional spring non-return valves for reasons of resistance in the context of the chemicals employed (paracetic acids come into contact with spring steel—not resistant). When using elastomer non-return valves or additional bypass circuits, a considerable extra expenditure (extra costs) for the added components would also have to be considered in addition to the disadvantageous hygienic properties. Advantageously, non-return valves are not required for the approach presented here.

The approach presented also does not require additional hardware components, e.g., non-return valves in the supply branch between the recirculation pump and the endoscope monitoring unit, and describes the method (on the process side) for identifying the channel branches. Through an initial software routine, the branched channels inside an endoscope are considered in all subsequent process steps in the case of a pulsation such that the reprocessing that is most effective for the rinsing device can take place without resurge effects in the recirculation circuit.

The rinsing device can detect, independently of the presence of an endoscope database, which channels of the loaded ware (endoscope) are connected to other channels of the load. In addition, the approach presented here allows a proper hygienic configuration for an air/water pulsation in a rinsing device and does away with the use of non-return valves in the rinsing circuit. The integration effort in the process is possible at the beginning of the rinsing process without extending the overall process time. The process reliability can be increased and there is no added mechanical stress for components located in the rinsing circuit such as pumps and/or the recirculation pump.

According to one embodiment, the method can identify a connection between the first and at least one third channel element located in the rinsing device, wherein, in the step of reading in, an additional pressure signal can be read in which represents an additional pressure in the third channel element, wherein, in the step of detecting, the connection between the first and the at least third channel element can be detected when the additional pressure is at a predetermined ratio to the testing pressure and/or above a threshold. This offers the advantage that an additional connection to a third channel element in the rinsing device can be tested and/or detected simply and efficiently.

According to one embodiment, the method can identify a connection between the second and at least the third channel element located in the rinsing device, wherein, in the step of applying, a second testing pressure can be applied to the second channel element, wherein, in the step of detecting, the connection between the second and the at least third channel element can be detected when the additional pressure is at a predetermined ratio to the additional testing pressure and/or above an additional threshold. This offers the advantage that a connection between the second and at least the third channel element can be tested and/or detected simply and efficiently.

According to one embodiment, before the step of applying the second testing pressure to the second channel element, the testing pressure can be released from the first channel element and/or at least reduced. This can increase the process reliability and improve a detection of a fluidic connection.

According to one embodiment, the method can have a step of storing information about the presence of the connection in a table, such as wherein the rows and the columns each represent one of the channel elements. This offers the advantage that the rinsing device can detect with simple means which channel elements are connected to other channel elements.

According to one embodiment, in the step of applying, compressed air and/or a liquid can be pumped into the first channel element to build up the testing pressure. Especially when using a cleaning liquor, the fluidic connection can be detected in such a procedure quickly and easily, wherein, in this case, a first cleaning of the channel element can already be executed and the cleaning then also be completed more quickly.

According to another embodiment, in the step of applying, the testing pressure can be applied into a medical device as a channel element, such as into an endoscope element and/or wherein, in the step of reading in, a pressure in a second medical device as a second channel element, such as in a second endoscope element can be read in. This offers the advantage that endoscope elements can be cleaned or reprocessed optimally and with little effort.

Furthermore, according to one embodiment, in the step of applying, the testing pressure can be applied to the channel element using a 3/2-way valve. This offers the advantage that the path of the volume flow can be controlled optimally and with technically simple means.

In the step of applying, according to one embodiment the testing pressure can be applied to the channel element by a pressure connection of a pulsation module and wherein, in the step of reading in, the pressure signal can be read in by a pressure sensor of the pulsation module, such as wherein the pressure sensor and the pressure connection are arranged in a common pulsation module housing. This can increase the process reliability.

The steps of applying, reading in, and/or detecting can be executed according to one embodiment when a recirculation pump for recirculating a treatment liquor is switched on or switched off. This offers the advantage that the method can be performed independently from the recirculation pump and thus no additional mechanical stress for the components located in the rinsing circuit, such as the recirculation pump, arises. Alternatively, the detection can also take place during a recirculation so that a faster cleaning of the channel elements can be achieved.

According to one embodiment, a method for cleaning a channel element comprises a step of conveying a treatment liquor through the first and/or second channel element, in response to the connection detected in the mentioned method. This offers the advantage that the channel element can be reprocessed hygienically. In addition, the reprocessing can be performed without the use of a non-return valve.

A control device (such as a controller, CPU, etc.) can execute and/or control the steps of one of the methods in corresponding units.

According to one embodiment, a rinsing device can have the control device, a rinsing chamber, and at least one rinsing basket.

The approach presented here also creates a control device which is configured to perform, control, or respectively implement the steps of a version of one of the methods presented here in corresponding devices. The object can also be solved quickly and efficiently by this embodiment version the form of a control device.

The control device can be configured to read in input signals and to determine and provide output signals using the input signals. An input signal can repro resent, for example, a sensor signal that can be read in via an input interface of the control device. An output signal can represent a control signal or a data signal which can be provided at an output interface of the control device. The control device can be configured to determine the output signals using a processing rule implemented in hardware or software. For example, the control device can comprise a logic circuit, an integrated circuit, or a software module for this purpose and, for example, be realized as a discrete part or be comprised by a discrete part.

A computer program product or computer program with program code is also advantageous, which can be stored on a machine-readable carrier or storage medium such as a semiconductor memory, a hard drive memory, or an optical memory. If the program product or program is executed on a computer or a device, the program product or program can be used to perform, implement, and/or control the steps of the methods according to one of the previously described embodiments.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general idea of the invention, based on exemplary embodiments in reference to the drawings, whereby we expressly refer to the drawings with regard to the disclosure of all details that are not explained in greater detail in the text.

An exemplary embodiment is shown purely schematically in the drawings and is described in more detail in the following. In the figures

FIG. 7 illustrates an output matrix of an exemplary embodiment of a method for identifying a connection;

FIG. 10 illustrates a flow chart of an exemplary embodiment of a method for cleaning a channel element.

DETAILED DESCRIPTION

Figure 1:
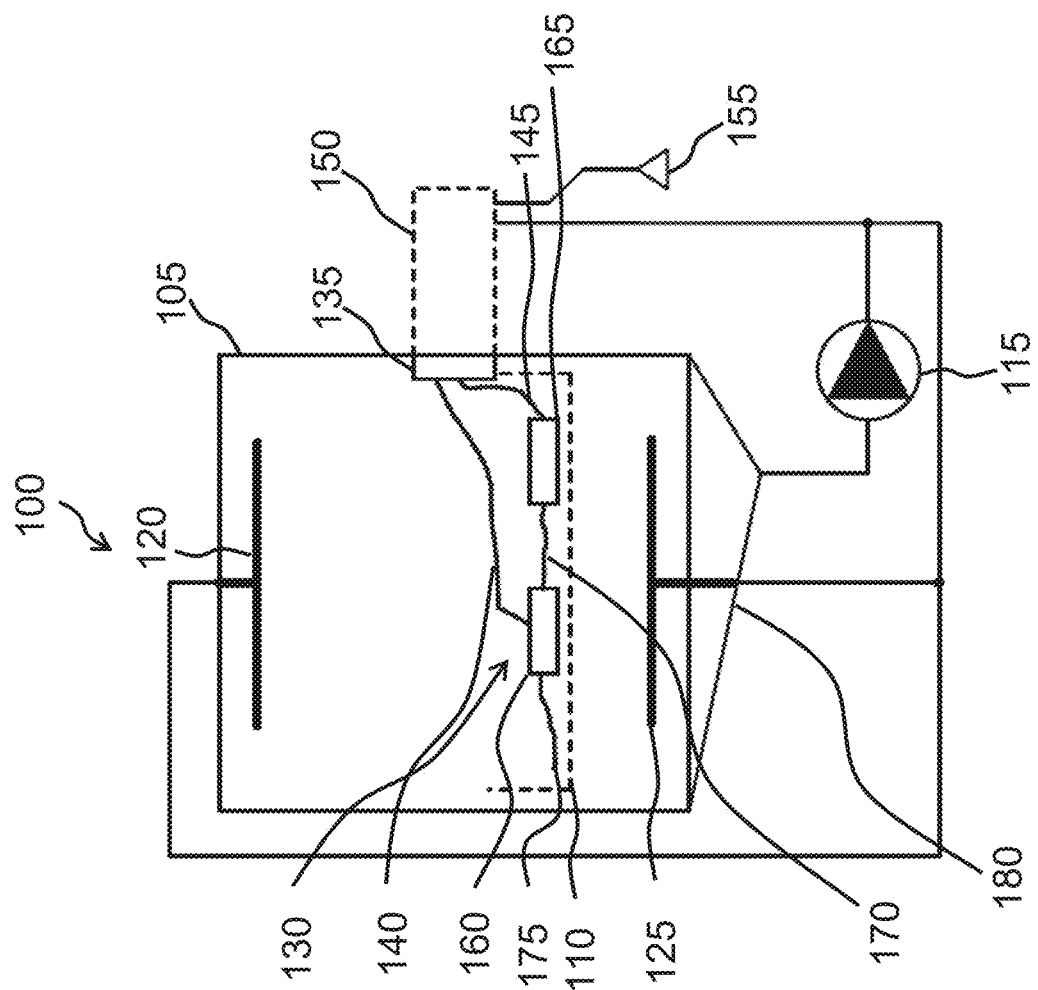
FIG. 1 illustrates a diagram of an exemplary embodiment of a rinsing device.

FIG. 1 shows a diagram of an exemplary embodiment of a rinsing device 100 according to an exemplary embodiment. The rinsing device 100 can be a cleaning and disinfecting device for cleaning, disinfecting, and reprocessing minimally invasive surgical instruments, for example, endoscopes or the like. The rinsing device 100 has a rinsing chamber 105. The rinsing chamber 105 is configured, for example, to receive a rinsing basket 110. For example, a recirculation pump 115 is located below the rinsing basket 110 and is configured to pump a liquid, such as a treatment liquor, through lines into the rinsing chamber 105 to the rinsing basket 110.

Optionally, the rinsing device 100 has two spray arms 120, 125 through which the treatment liquor is sprayed into the rinsing chamber 105. In this case, for example, a first spray arm 120 is located on a ceiling of the rinsing chamber 105 above the rinsing basket 110 and a second spray arm 125 is located on a floor of the rinsing chamber 105 below the rinsing basket 110.

The rinsing basket 105 is provided to receive cleaning ware 130, according to one exemplary embodiment a medical device, for cleaning and additionally or alternatively for disinfecting. FIG. 1 schematically shows cleaning ware 130 in the form of an endoscope arranged in the rinsing basket 105. To attach the cleaning ware 130 to the rinsing device 100, the rinsing basket 110 has an adapter device 135. For example, the adapter device 135 is configured as an adapter plate and fastened to a wall of the rinsing basket 110. The cleaning ware 130 is fastened, for example, with two hoses 140, 145 to the corresponding adapter device 135. For this purpose, the adapter device 135 has connecting pieces, by which the hoses 140, 145 can be connected.

To attach the cleaning ware 130 via the adapter device 135 to the rinsing device 100, the adapter device 135 is coupled to a pulsation module 150. In this state, the treatment liquor can be conducted through the pulsation module 150 to the adapter device 135 and from the adapter device 135 to the cleaning ware 130. Furthermore, the rinsing device 100 has a compressed air supply 155 which is configured to conduct compressed air into the cleaning ware 130. Similarly to the treatment liquor, the compressed air is conducted via the pulsation module 150 to the cleaning ware 130. The hoses 140, 145 are configured to conduct the treatment liquor and the compressed air through the pulsation module 150 to the adapter device 135 and from the adapter device 135 to the cleaning ware 130.

The cleaning ware 130 comprises, for example, an operating part 160 and a connection plug 165, wherein the operating part 160 and the connection plug 165 are connected to each other via a connecting element 170. The operating part 160 is coupled to the adapter device 135 with the hose 140, while the connection plug 165 is coupled to the adapter device 135 with the hose 145. The operating part 160 has, for example, a distal end 175. A sump 180, for example, is located below the rinsing chamber 105 and is configured to feed the recirculation pump 115 with the treatment liquor. Before a cleaning and/or rinsing process, it is identified, for example, whether a connection exists between the connection plug 165 and the operating element 160.

For this purpose, a testing pressure is applied to the connection plug 165, for example, which is formed as a first channel element 165. The testing pressure is conducted from the compressed air supply 155 through the pulsation module 150 via the hose 145 to the first channel element 165. Then, a pressure signal is read which represents a pressure in the operating element 160, which is formed as a second channel element 160. When the pressure is at a predetermined ratio to the testing pressure and/or is above a threshold, a connection between the first 165 and the second channel element 160 is detected.

The described method is employed inside a rinsing device 100, which can also be referred to as a cleaning and disinfecting device (CDD-E), which feeds a sump 180 of the one recirculation pump 115 via a rinsing chamber 105, which can also be referred to as a rinsing space, which recirculation pump supplies both the first spray arm 120, which can also be referred to as the upper rinsing arm, and the second spray arm 125, which can also be referred to as the lower rinsing arm. In addition, the outlet of the recirculation pump 115 is connected to a pulsation module 150 by a liquor connection. The pulsation module 150 also has at least one compressed air supply 155, which has a higher pressure level compared to the liquor connection. The cleaning ware 130, which can also be referred to as the loaded ware, meaning the endoscope, comprising a connection plug 165, an operating part 160, a connection 170 which connects the connection plug 165 to the operating part 160, an endoscope hose which ends at the distal end 175, and a hose 135, which can also be referred to a connection, from the operating part 160 to the adapter device 135 as well as a hose 145, which can also be referred to as a connection, from the connection plug 165 to the adapter device 135, wherein the two hoses 140, 145 to the adapter device 135 are used to connect the endoscope to the rinsing device 100.

The reprocessing process inside the rinsing device 100 comprises, for example, of the following:
performing a leak-tightness test and starting monitoring for subsequent steps;
pre-rinsing phase (water inlet, rinsing, water outlet);

cleaning phase (water inlet and metering of cleaning chemicals and heating, rinsing, water outlet);

intermediate rinsing (water inlet, rinsing, water outlet);

disinfecting phase (water inlet and metering of disinfecting chemicals and heating, rinsing, water outlet);

post-rinsing 1 (water inlet, rinsing, water outlet);

post-rinsing 2 (water inlet and heating if drying follows, rinsing, water outlet); and final drainage or drying The described method is executed during the reprocessing in the cleaning device 100, for example, only once, if possible at the beginning of the reprocessing, e.g., in parallel with performing the leak-tightness test and monitoring for subsequent steps or during the pre-rinsing phase.

The described information is used, for example, to perform a more effective drainage between the rinsing phases, during the final drainage or during the drying of the inner channels. It is thus possible to also reprocess third-party endoscopes with the rinsing device 100 so that an optimized drying or drainage that is adapted to the present endoscope type takes place. The same applies to the flow measurement. Branched channels of third-party endoscopes or endoscopes of which the branching information is initially not known are measured in parallel during the flow measurement of a branched channel.

Figure 2:
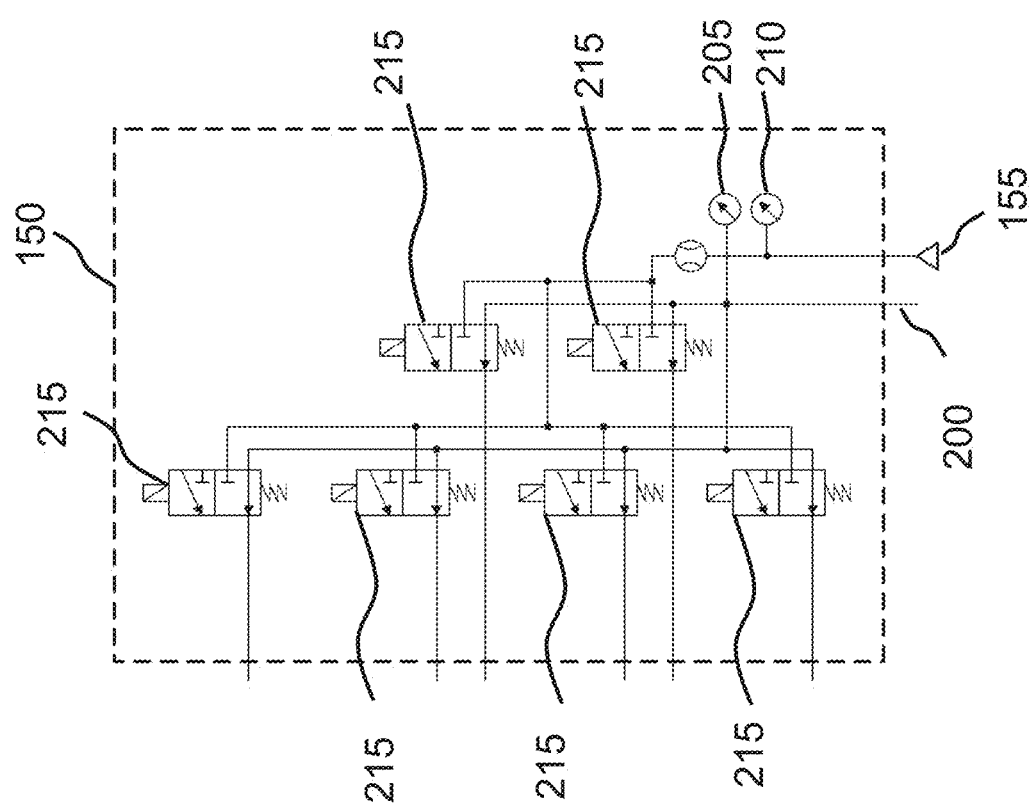
FIG. 2 illustrates a diagram of a pulsation module for an exemplary embodiment of a rinsing device.

FIG. 2 shows a diagram of a pulsation module 150 for an exemplary embodiment of a rinsing device. The pulsation module 150 can be the pulsation module 150 described in FIG. 1. The pulsation module 150 is installed, for example, in a rinsing device. A compressed air supply 155, for example, is arranged below the pulsation module 150 and applies compressed air or respectively testing pressure to the valves 215. The treatment liquor, for example, flows through the valves 215, which takes place via a liquor connection 200. For example, two pressure sensors 205, 210 are arranged in the pulsation module 150, wherein the one pressure sensor 205 is configured as a liquor pressure sensor and the second pressure sensor 210 is configured as a compressed air sensor.

The pulsation module 150 comprises a number of 3/2-way valves 215 which, in the one switching position, ensure that an endoscope channel is supplied with treatment liquor, which can also be referred to as rinsing liquor, by the recirculation pump. In the other switching position, compressed air is applied to the respective endoscope channel and the connection to the liquor supply is interrupted. Both the compressed air input and the liquor supply of the pulsation module 150 are connected to a pressure sensor 205, 210.

Figure 3:
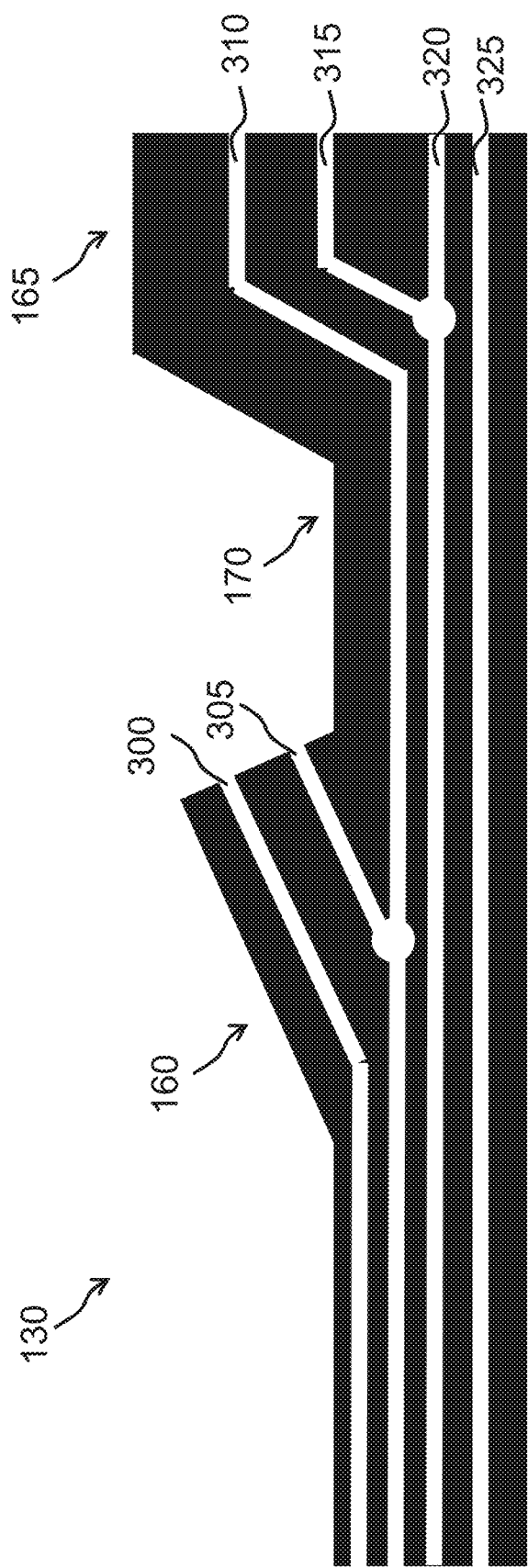
FIG. 3 illustrates a diagram of cleaning ware for use in an exemplary embodiment of a rinsing device.

FIG. 3 shows a diagram of cleaning ware 130 for use in an exemplary embodiment of a rinsing device 100.

The cleaning ware 130 can be the cleaning ware 130 described in FIG. 1. The cleaning ware 130 is formed in FIG. 3, for example, as an endoscope. FIG. 3 shows which channels are connected to which other channels. The cleaning ware 130 comprises, for example, of the operating element 160 and the connection plug 165.

The operating element 160 has, for example, two channel elements 300, 305 and is coupled to the connection plug 165 via the connection 170. The connection plug 165 has, for example, four channel elements 310, 315, 320, 325.

According to one exemplary embodiment, the channel element 305 of the operating element 160 is connected to the channel element 310 of the connection plug. The channel element 315 is connected to the channel element 320.

An example of an algorithm using the pulsation module shown in FIG. 2 runs, for example, as follows: The pump in the rinsing device runs during the check of the connections of the channel elements with reduced rotational speed in a target pressure range of, for example, DSF=450 . . . 550 mbar. The pressure level is, for example, DSL=1450 to 1550 mbar.

A control variable i=1 is set and a limit value or respectively tolerance of the measurement values is established, e.g., Tol=100 mbar. Then, the first channel element 300 is checked for a connection to an additional channel element. For this purpose, a valve V1 in the first channel element 300 is switched on or respectively through (i=1). It is tested whether an increased pressure in the first channel element 300 is measurable at a pressure sensor. This is not the case, which means that the first channel element 300 has no connection to an additional channel element. After the first channel element 300 is checked for a connection, the valve V1 of the first channel element 300 is switched off again. Now i=i+1 is set and the valve V2 of the second channel element 305 is switched on. It is tested whether a pressure in the second channel element 305 is measurable at the pressure sensor. In this case, a pressure is measurable, so that it is concluded that the second channel element 305 has a (fluidic) connection to an additional channel element. It is then tested which channel element the second channel element 305 is connected to. For this purpose, a second control variable j=1 is set and the valve V1 of the first channel element 300 is switched on. It is now tested whether the pressure in the pressure sensor normalizes again to a target value, for example 450 . . . 550 mbar. This is not the case. The second channel element 305 is thus not connected to the first channel element 300. Therefore, the valve V1 of the first channel element 300 is switched off, since i is not equal to j. Now j=j+1 (j=2) is set and the valve V2 of the second channel element 305 is switched on, or respectively it was already switched on before. It is then tested whether the pressure in the pressure sensor normalizes again to its target value, 450 . . . 550 mbar. This is not the case. The second channel element 305 is not only (fluidically) connected to the second channel element 305. The valve V2 of the second channel element 305 is switched off when i is not equal to j. Since i is equal to j, the valve V2 of the second channel element 305 remains switched on. Now j=j+1 (j=3) is set and the third channel element 310 is switched on. It is then tested whether the pressure in the pressure sensor normalizes again to its target value, 450 . . . 550 mbar. The pressure normalizes again so that the second channel element 305 of the operating element 160 is connected to the third channel element 310 of the connection plug 165. Now a matrix KV(2; 3)=1 is set. The matrix means that a connection between the second channel element 305 and the third channel element 310 exists. The valve V3 of the third channel element 310 is then switched off, since i is not equal to j. Now j=j+1 (j=4) is set and the fourth channel element 315 is switched on. The connections of the channel elements 315, 320 and 325 are tested (i=2) until j=6. Then the valve V2 of the second channel element 305 is switched off and i=i+1 is set and the valve V3 of the third channel element 310 is switched on. It is now tested whether an increased pressure is measurable at the pressure sensor. This is the case, so that it is concluded that the second channel element 305 has a (fluidic) connection to an additional channel element. This is already known from the previous checks.

Figure 4:
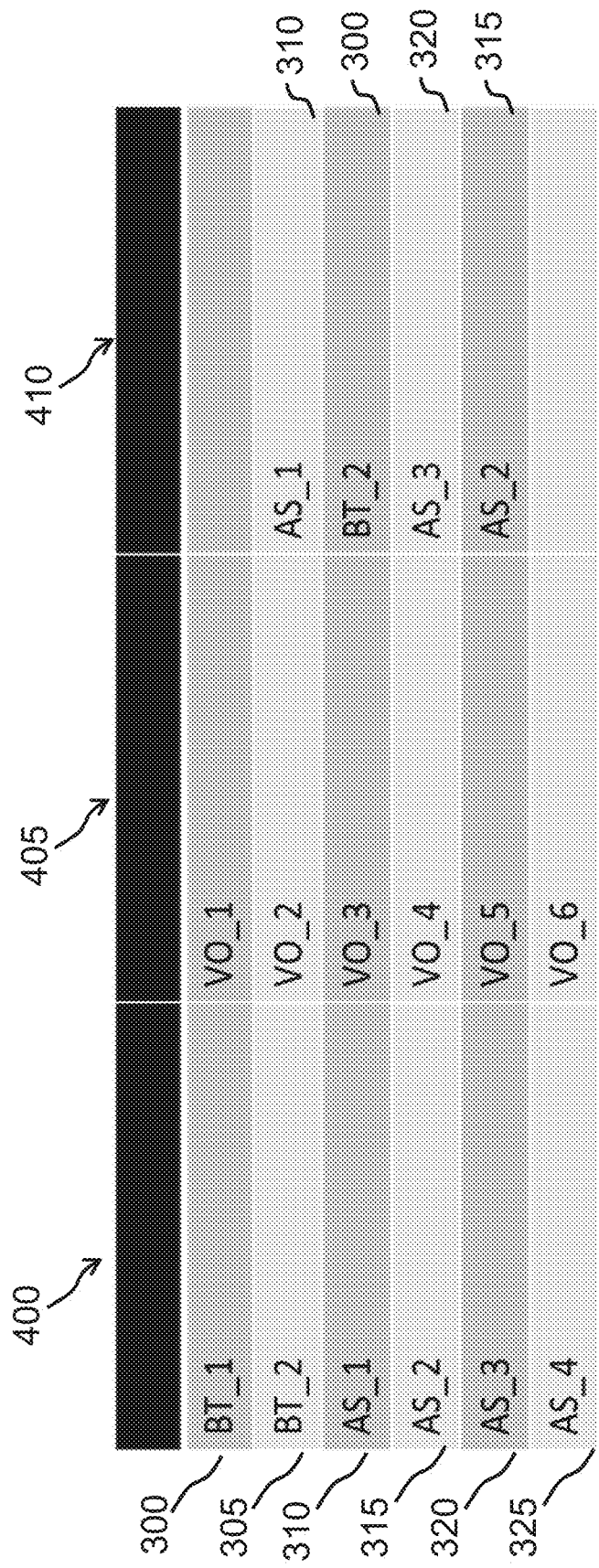
FIG. 4 illustrates a table with an overview of connections between channel elements for use in an exemplary embodiment of a rinsing device.

FIG. 4 shows a table with an overview of connections between channel elements for use in an exemplary embodiment of a rinsing device 100. In this case, it is a connection table of the connections of the cleaning ware from FIG. 3. The channel elements are listed in the left column 400. The channel elements that are connected to the channel elements from the left column 400 are listed in the right column 410. The connections via which individual channel elements are connected to each other are listed in the middle column 405. For example, the first channel element 300 has a connection but is not connected to an additional channel element. The second channel element 305 has a connection and is branched via this connection with the third channel element 310. The third channel element 310, on the other hand, is branched via a connection with the second channel element 305. The fourth channel element 315 is branched via a connection to the fifth channel element 320. The fifth channel element 320, on the other hand, is branched via a connection with the fourth channel element 315. The sixth channel element 325 has a connection but is not branched with another channel element.

Figure 5:
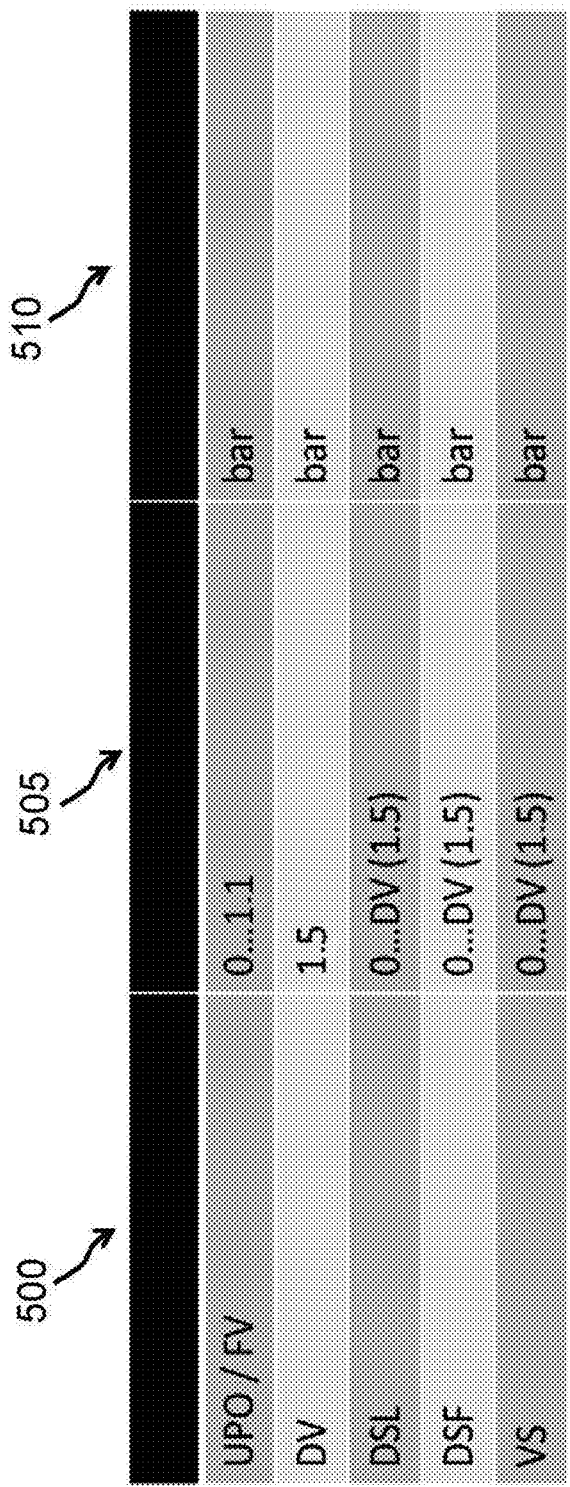
FIG. 5 illustrates a table with an overview of pressure levels of relevant components of an exemplary embodiment of a rinsing device.

FIG. 5 shows a table with an overview of pressure levels of relevant components of an exemplary embodiment of a rinsing device 100. The components are listed in the left column 500, the various pressure levels are listed in the middle column 505, and the pressure unit is given in the right column 510. The output of the recirculation pump 115 or respectively the liquor connection 200 has a pressure level of, for example, 0 . . . 1.1 bar. The compressed air supply 155 has a pressure level of, for example, 1.5 bar. The compressed air sensor 210, the liquor pressure sensor 205, and the volume flow 515 each have a pressure level of, for example, 1.5 bar.

Figure 6:
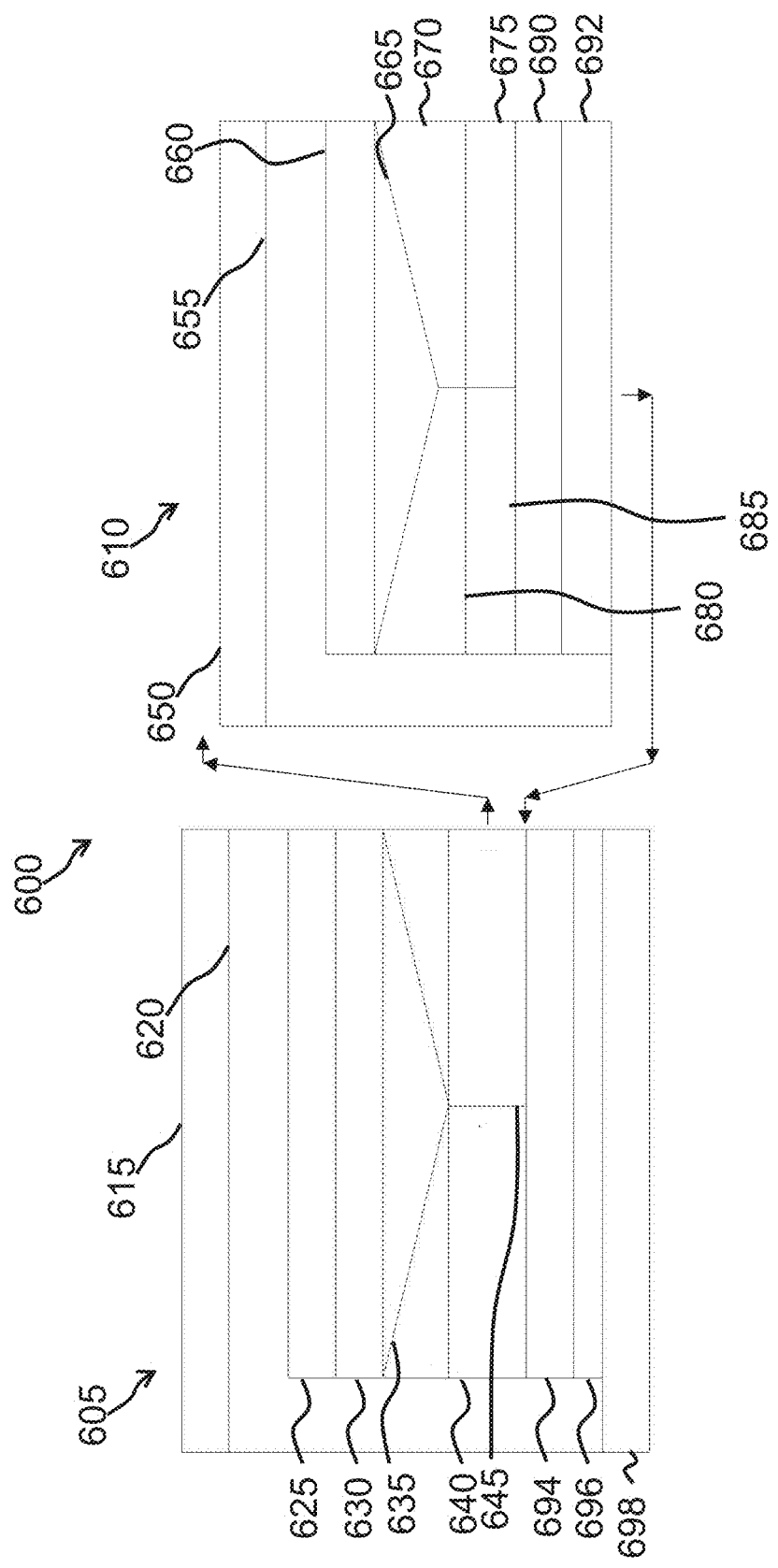
FIG. 6 illustrates a structure chart of an exemplary embodiment of a method for identifying a connection.

FIG. 6 shows a structure chart 600 of an exemplary embodiment of a method for identifying a connection. The structure chart 600 has a left block 605 and a right block 610. The channel branches are detected in the left block 605 and the channel branches are checked in the right block 610. The method starts in that an instruction 615 takes place which sets i=1 and establishes the tolerance range of the pressure, for example 100 mbar. Then the instruction 620 is established which signifies that the following instructions are performed or respectively repeated as long as i<=6 applies. Next, the instruction 625 follows, in which the liquor pressure sensor_i=liquor pressure sensor; is set. When the recirculation pump is switched off, then the following applies: liquor pressure sensor_i=0. In the instruction 630, Vi=1 applies; the valve Vi of the first channel element is switched on. Then the condition 635 follows, in which it is tested whether the liquor pressure sensor is greater than the liquor pressure sensor_i plus the tolerance range. If the condition is not true, it is identified in the instruction 640 that the first channel element has no branch to an additional channel element. If the condition 635 is true, the function invocation to check the channel branches takes place and it jumps to block 610 in which the channel branches are checked. For this purpose, the instruction 650 j=1 is set, followed by the instruction 655 that the following instructions are performed or respectively repeated as long as j<=6 applies. Then the instruction 660 follow, in which the valve Vj of the second channel element is switched on; the valve Vi of the first channel element is already active.

Then the condition 665 follows, in which it is tested whether the liquor pressure sensor is smaller than the liquor pressure sensor_i plus the tolerance range. If the condition is not true, no channel branch is identified in the instruction 670. The corresponding matrix 675 is: Matrix_KV(i:j)=0. If the condition 665 is true, a branch between the first channel element and the second channel element is detected in the instruction 680. The corresponding matrix 685 is: Matrix_KV(i:j)=1. In the instruction 690, it means that when i is not equal to j, Vj=0. Thereafter, the valve Vj of the second channel element is switched off. In the instruction 692, j=j+1 is set. Then it jumps again to block 605. In block 605, Vi=0 is set in the instruction 694 and thus the valve Vi of the first channel element is switched off. In block 696, i=i+1 is set and then the matrix Matrix_KV(6×6) is emitted in the instruction 698 and the method for identifying a connection between a first and at least one second channel element located in a rinsing device is completed.

The method can be performed when the recirculation pump is switched on or switched off. The usual configuration inside of a rinsing device (CDD-E) for performing the method looks as follows: The pump pressure is smaller than the pressure of the compressed air supply. The method tests each channel one after the other, as long as the i<=6 loop applies in the instruction 620, whether a connection to another channel exists, when the liquor pressure sensor (DSF) possesses a higher pressure than its usual pressure value, when the recirculation pump is switched on or off. This takes place through the check 635 DSF>=DSF_i+Tol.

If this feedback is present, by meeting the previous testing condition, in the instruction 635 with the valve Vi switched within the first loop, it is now checked which channel the active channel is connected to. This takes place via an additional, subordinate loop (instruction 655, as long as j<=6) which is run through after the function invocation check_branch(i). Here, an additional valve j is always added to the currently active valve Vi one after the other in the instruction 660. When the testing condition DSF<=DSF_i+Tol is met, meaning the pressure in the liquor supply normalizes again, when two valves are active in parallel, it can always be assumed that the current channel i is connected to the channel j. To document this, a "1" is set at the respective location in an output matrix Matrix_KV(i,j)→channel i is connected to channel j. At all other locations with which channel i has no connection to other channels (j), a 0 is set.

Based on the Matrix_KV(i,j) 675, which possesses the dimension n×n (meaning, in our example, 6×6), the cleaning and disinfecting device (CDD-E) can now always apply compressed air in parallel to the channels that are connected to each other in all following drainage routines so that, in contrast to a sequential application of compressed air to individual channels, resurge effects on the liquor supply and thus the recirculation pump no longer occur via a channel branch (e.g., FIG. 3, the second channel element is connected to the third channel element) in a later drainage step.

FIG. 7 shows an output matrix of an exemplary embodiment of a method for identifying a connection. In this case, these can be the connections described in FIG. 3, FIG. 4 and FIG. 6 between individual channel elements.

The output matrix is Matrix_KV(6×6) and is shown in a table in FIG. 7. For the row 705, the following applies: 0 0 0 0 0 0. This means that the first channel element has no channel branch. For the row 710, the following applies: 0 0 1 0 0 0. This means that the second channel element has one channel branch with the third channel element. The row 715 represents a channel branch between the third channel element and the second channel element. The row 720 represents a channel branch of the fourth channel element with the fifth channel element. In row 725, a channel branch of the fifth channel element with the fourth channel element is shown. The row 730 reflects that the sixth channel element has no channel branch.

Figure 8:
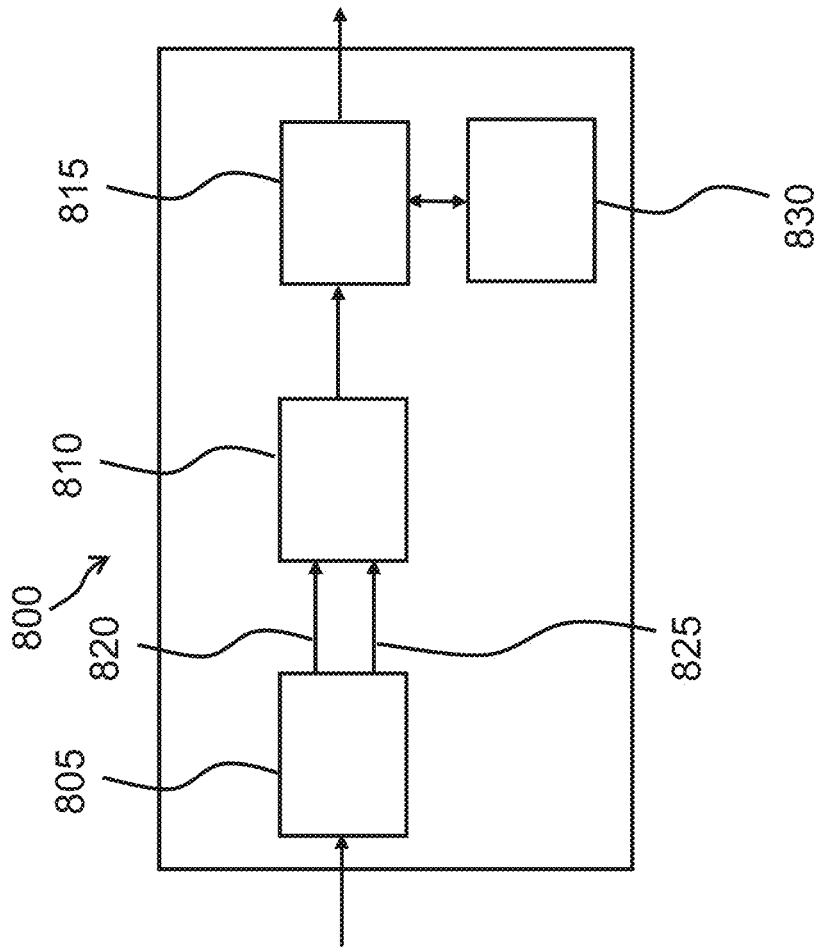
FIG. 8 illustrates a block diagram of a device according to an exemplary embodiment.

FIG. 8 shows a block diagram of a control device 800.

The control device 800 has an application device 805, a reading-in device 810, and a detection device 815. The application device 805 is configured to apply a testing pressure to the first channel element. The reading-in device 810 is configured to read in a pressure signal 820, wherein the pressure signal 820 represents a pressure in the second channel element. The detection device 815 is configured to detect the connection between the first and the at least second channel element when the pressure is at a predetermined ratio to the testing pressure and/or above a threshold.

According to one exemplary embodiment, the reading-in device 810 is configured to read in an additional pressure signal 825 to identify a connection between the first and at least one third channel element located in the rinsing device. The additional pressure signal 825 represents an additional pressure in the third channel element. The detection device 815 is further configured to detect the connection between the first and the at least third channel element when the additional pressure is at a predetermined ratio to the testing pressure and/or above a threshold.

According to one exemplary embodiment, the application device 805 is configured to apply a second testing pressure to the second channel element to identify a connection between the second and at least the third channel element located in the rinsing device. In response to this, the connection between the second and the at least third channel element is detected in the detection device 815 when the additional pressure is at a predetermined ratio to the additional testing pressure and/or above an additional threshold.

According to another exemplary embodiment, the control device 800 has a storage device 830 which is configured to store information about the presence of the connection in a table. In this case, the rows and the columns each represent one of the channel elements.

Figure 9:
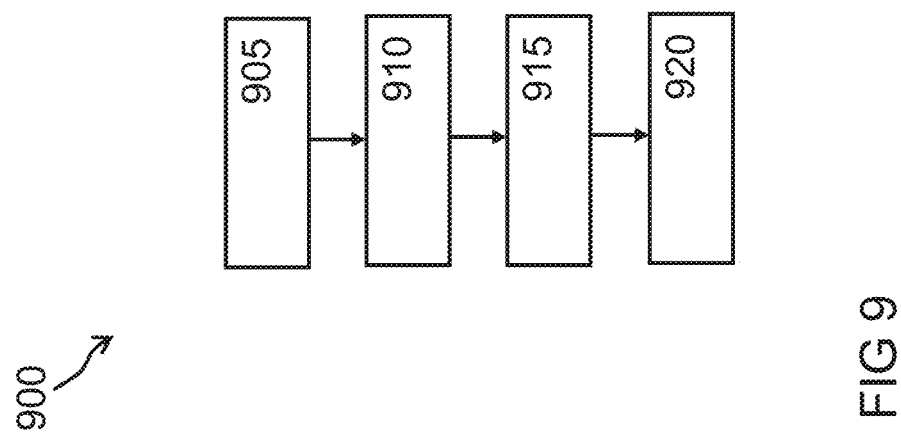
FIG. 9 illustrates a flow chart of an exemplary embodiment of a method for identifying a connection between a first and at least one second channel element located in a rinsing device.

FIG. 9 shows a flow chart of an exemplary embodiment of a method 900 for identifying a connection between a first and at least one second channel element located in a rinsing device. The method 900 has a step 905 of applying a testing pressure to the first channel element, and a step 910 of reading in a pressure signal which represents a pressure in the second channel element and a step 915 of detecting the connection between the first and the at least second channel element when the pressure is at a predetermined ratio to the testing pressure and/or above a threshold. In the step 905 of applying, compressed air and/or a liquid, for example, is pumped into the first channel element to build up the testing pressure. Furthermore, in the step 905 of applying, the testing pressure is applied in a medical device as a channel element, such as in an endoscope element. In the step 910 of reading in, a pressure in a second medical device as a second channel element, such as in a second endoscope element, is then read in. In the step 905 of applying, the testing pressure is applied to the channel element using, for example, a 3/2-way valve. According to one exemplary embodiment, in the step 905 of applying, the testing pressure is applied to the channel element by a pressure connection of a pulsation module. In the step 910 of reading in, the pressure signal is then read in by a pressure sensor of the pulsation module, such as wherein the pressure sensor and the pressure connection are arranged in a common pulsation module housing.

According to one exemplary embodiment, the method 900 is configured to identify a connection between the first and at least one third channel element located in the rinsing device. For this purpose, in the step 910 of reading in, an additional pressure signal which represents an additional pressure in the third channel element is read in. In the step 915 of detecting, the connection between the first and the at least third channel element is then detected when the additional pressure is at a predetermined ratio to the testing pressure and/or above a threshold.

According to one exemplary embodiment, the method 900 is configured to identify a connection between the second and at least the third channel element located in the rinsing device. For this purpose, in the step 915 of applying, a second testing pressure is applied to the second channel element. In the step 915 of detecting, the connection between the second and the at least third channel element is then detected when the additional pressure is at a predetermined ratio to the additional testing pressure and/or above an additional threshold.

According to one exemplary embodiment, before the step 905 of applying the second testing pressure to the second channel element, the testing pressure is released from the first channel element and/or at least reduced.

According to one exemplary embodiment, the method 900 has a step 920 of storing information about the presence of the connection in a table, such as wherein the rows and the columns each represent one of the channel elements.

The steps of applying 905, reading in 910, and/or detecting 915 are executed when a recirculation pump for recirculating a treatment liquor is switched on or switched off.

FIG. 10 shows a flow chart of an exemplary embodiment of a method 1000 for cleaning a channel element. The method 1000 comprises a step 1005 of conducting a treatment liquor through the first and/or second channel element in response to the connection detected by a method in FIG. 9.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for identifying a connection between a first channel and at least one second channel located in a rinsing device, wherein the method comprises:
   applying a first testing pressure to the first channel;
   receiving a first pressure signal representing a first pressure in the at least one second channel;
   detecting the connection between the first channel and the at least second channel when the first pressure is one or more of:
      at a predetermined first ratio to the testing pressure; and
      above a predetermined first threshold; and
   identifying a connection between the first channel and at least one third channel located in the rinsing device, wherein the receiving comprises, receiving a second pressure signal representing a second pressure in the third channel, and the detecting comprises detecting the connection between the first channel and the at least third channel when the second pressure is one or more of:
      at a predetermined second ratio to the testing pressure; and
      above a predetermined second threshold.

2. The method according to claim 1, further comprising identifying a connection between the at least one second channel and the at least the third channel wherein the applying comprises, applying a second testing pressure to the at least one second channel element, and the detecting comprises, detecting the connection between the at least one second channel and the at least third channel when the second pressure is one or more of:
at a predetermined ratio to the second testing pressure; and
above the second threshold.

3. The method according to claim 2, wherein, before the applying of the second testing pressure to the second channel, the testing pressure is at least reduced from the first channel.

4. The method according to claim 1, further comprising storing information in a table about a presence of the connection.

5. The method according to claim 4, wherein the table comprises rows and the columns each representing one of the first channel and the at least one second channel.

6. The method according to claim 1, wherein, during the applying, one or more of compressed air and a liquid is pumped into the first channel to build up the testing pressure.

7. The method according to claim 1, wherein, the applying comprises, applying the first testing pressure is applied into a first medical device as the first channel.

8. The method according to claim 7, wherein, of the receiving comprises, receiving a pressure in a second medical device as the second channel.

9. The method according to claim 1, wherein, the applying comprises, applying the first testing pressure to the first channel and the at least one second channel using a 3/2-way valve.

10. The method according to claim 1, wherein, the applying comprises, applying the first testing pressure to the first channel and the at least one second channel by a pressure connection of a pulsation module and wherein, the receiving comprises, receiving the first pressure signal by a pressure sensor of the pulsation module.

11. The method according to claim 10, wherein the pressure sensor and the pressure connection are arranged in a common pulsation module housing.

12. He method according to claim 1, wherein one or more of the applying, receiving and detecting are executed whether a recirculation pump for recirculating a treatment liquor is switched on or switched off.

13. The method according to claim 1, further comprising conducting a treatment liquor through one or more of the first channel and the second channel in response to the detected connection.

14. A control device for identifying a connection between a first channel and at least one second channel located in a rinsing device, the control device comprising:
a controller comprising hardware, the controller being configured to:
control a first testing pressure to be applied to the first channel;
receive a first pressure signal representing a first pressure in the at least one second channel;
determine the connection between the first channel and the at least second channel when the first pressure is one or more of:
at a predetermined first ratio to the testing pressure; and
above a predetermined first threshold; and
identify a connection between the first channel and at least one third channel located in the rinsing device, wherein the receiving comprises, receiving a second pressure signal representing a second pressure in the third channel, and the detecting comprises detecting the connection between the first channel and the at least third channel when the second pressure is one or more of:
at a predetermined second ratio to the testing pressure; and
above a predetermined second threshold.

15. A rinsing device comprising:
the control device according to claim 14 for identifying the connection between the first channel and the at least one second channel located in the rinsing device.

16. A computer-readable device for identifying a connection between a first channel and at least one second channel located in a rinsing device, the computer-readable device storing instructions that cause a computer to at least perform:
controlling a first testing pressure to be applied to the first channel;
receiving a first pressure signal representing a first pressure in the at least one second channel;
determining the connection between the first channel and the at least second channel when the first pressure is one or more of:
at a predetermined first ratio to the testing pressure; and
above a predetermined first threshold; and
identifying a connection between the first channel and at least one third channel located in the rinsing device, wherein the receiving comprises, receiving a second pressure signal representing a second pressure in the third channel, and the detecting comprises detecting the connection between the first channel and the at least third channel when the second pressure is one or more of:
at a predetermined second ratio to the testing pressure; and
above a predetermined second threshold.

17. A method for identifying a connection between a first channel and at least one second channel located in a rinsing device, wherein the method comprises:
applying a first testing pressure to the first channel;
receiving a first pressure signal representing a first pressure in the at least one second channel; and
detecting the connection between the first channel and the at least second channel when the first pressure is one or more of:
at a predetermined first ratio to the testing pressure; and
above a predetermined first threshold;
wherein, the applying comprises, applying the first testing pressure to the first channel and the at least one second channel by a pressure connection of a pulsation module and wherein, the receiving comprises, receiving the first pressure signal by a pressure sensor of the pulsation module.

18. A control device for identifying a connection between a first channel and at least one second channel located in a rinsing device, the control device comprising:
a controller comprising hardware, the controller being configured to:
control a first testing pressure to be applied to the first channel;
receive a first pressure signal representing a first pressure in the at least one second channel; and
determine the connection between the first channel and the at least second channel when the first pressure is one or more of:
at a predetermined first ratio to the testing pressure; and
above a predetermined first threshold;

wherein, the applying comprises, applying the first testing pressure to the first channel and the at least one second channel by a pressure connection of a pulsation module and wherein, the receiving comprises, receiving the first pressure signal by a pressure sensor of the pulsation module.

19. A computer-readable device for identifying a connection between a first channel and at least one second channel located in a rinsing device, the computer-readable device storing instructions that cause a computer to at least perform:
controlling a first testing pressure to be applied to the first channel;
receiving a first pressure signal representing a first pressure in the at least one second channel; and
determining the connection between the first channel and the at least second channel when the first pressure is one or more of:
at a predetermined first ratio to the testing pressure; and
above a predetermined first threshold;
wherein, the applying comprises, applying the first testing pressure to the first channel and the at least one second channel by a pressure connection of a pulsation module and wherein, the receiving comprises, receiving the first pressure signal by a pressure sensor of the pulsation module.

* * * * *